United States Patent [19]

Zierke et al.

[11] Patent Number: 5,194,441
[45] Date of Patent: Mar. 16, 1993

[54] 3-SUBSTITUTED PYRIDINES

[75] Inventors: Thomas Zierke, Boehl-Iggelheim; Bernhard Zipperer, Dirmstein; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 633,773

[22] Filed: Dec. 21, 1990

[30] Foreign Application Priority Data

Dec. 29, 1989 [DE] Fed. Rep. of Germany ....... 3943277
Aug. 28, 1990 [DE] Fed. Rep. of Germany ....... 4027139

[51] Int. Cl.$^5$ .................. C07D 405/06; A61K 31/44
[52] U.S. Cl. .................... 514/336; 514/277; 546/283; 546/268; 546/341; 546/342
[58] Field of Search ............... 546/283; 514/336

[56] References Cited

U.S. PATENT DOCUMENTS 4,699,652 10/1987 Zehnder ............... 546/344
4,859,687 8/1989 Riebli ................ 546/270
4,940,483 7/1990 Kurahashi et al. ....... 546/283

FOREIGN PATENT DOCUMENTS 74018 3/1983 European Pat. Off. .

OTHER PUBLICATIONS

*Chem Abstracts*, vol. 80, No. 145 969 j (1974).
Tetrahedron, vol. 24, 1968, "Sterochemistry of the Ring Opening of Some Stilbazole Oxides", G. Berti et al., pp. 1959–1971.
Chelucci et al., CA 114: 207088c.
Zorin et al., CA 102: 220784y.
Clerici et al., CA 99: 70536x.
Stanbury et al., CA 99: 28601q.

*Primary Examiner*—Jane T. Fan
*Attorney, Agent, or Firm*—Oblon, Spivak, McClelland, Maier & Neustadt

[57] ABSTRACT

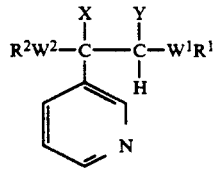

(X=OH; Y=—O—CHO, —O—CO—$W^3R^3$, —O—$SO_2$—$W^3R^3$ or X+Y=—O—CH($W^3R^3$)—O—, $^3O^3$CH($O^3W^4R^4$)—O—, —O—C($W^3R^3$)(O—$W^4R^4$)—O—; $W^1$-$W^4$=direct bond, —$CH_2$—, —$CH_2$—$CH_2$, —CH($CH_3$)—, —$CH_2O$—, —$CH_2S$—; $R^1$-$R^4$=unsubstituted or cylcoalkyl-substituted $C_1$-$C_6$-haloalkyl, $C_3$-$C_8$-cycloalkyl which is unsubstituted or substituted by 1–3 alkyl radicals, $C_1$-$C_4$-alkoxy- $C_1$-$C_4$-alkyl, $C_1$-$C_4$-alkylthio-$C_1$-$C_4$-alkyl, $C_2$-$C_6$-alkenyl, $C_2$-$C_6$-alkynyl, substituted or unsubstituted phenyl or naphthyl, substituted or unsubstituted 5-/6-membered heteroaryl with 1 to 3 heteroatoms;

$R^2$ is additionally H when X+Y=—O—CH($W^3R^3$)—O—, —O—CH(O—$W^4R^4$)—O— or —O—C($W^3R^3$)(O—$W^4R^4$)—O— and $W^2$=direct bond, except cis-1-(2,4-dichlorophenyl)-2-(pryid-3-yl)-1,2-epoxypropane, trans-1-(2,4-dichlorophenyl)-2-(pyrid-3-yl)-1,2-epoxypropane, 1-(2,4- dichlorophenyl)-2-(pryid-3-yl)-1,2-epoxybutane and 2,4-dichloro- α[1-hydroxy-1-(pyrid-3-yl)-ethyl]-benzyl methanesulfonate, and the N-oxides and the plant-tolerated mineral acid salts and metal complexes of I.

The compounds I are suitable as fungicides.

5 Claims, No Drawings

3-SUBSTITUTED PYRIDINES

The present invention relates to novel substituted pyridines of the formula I

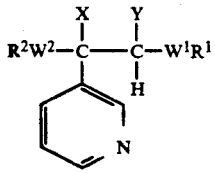

where
X is hydroxyl,
Y is —O—CHO, —O—CO—$W^3R^3$ or —O—$SO_2$—$W^3R^3$ or X and Y together are oxygen or a group

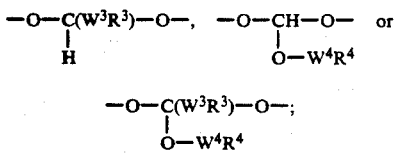

$$-O-\underset{\underset{O-W^4R^4}{|}}{C(W^3R^3)}-O-;$$

$W^1$–$W^4$ are each a direct bond or methylene, ethylene, methylmethylene, methyleneoxy or methylenethio, where the bond between the last two groups and the radicals $R^1$ to $R^4$ is via the oxygen or sulfur atom;
$R^1$–$R^4$ are each $C_1$–$C_6$-alkyl which may carry a $C_3$–$C_8$-cycloalkyl radical, or are each partially or completely halogenated $C_1$–$C_6$-alkyl, or are each $C_3$–$C_8$-cycloalkyl which may furthermore carry up to 3 $C_1$–$C_6$-alkyl groups, or are each $C_1$–$C_4$-alkoxy-$C_1$–$C_4$-alkyl, $C_1$–$C_4$-alkylthio-$C_1$–$C_4$-alkyl, $C_2$–$C_6$-alkenyl, $C_2$–$C_6$-alkynyl, phenyl or naphthyl, both of which may furthermore carry 1 or 2 of the following radicals: nitro, cyano, halogen, $C_1$–$C_4$-alkyl, partially or completely halogenated $C_1$–$C_4$-alkyl, $C_1$–$C_4$-alkoxy, $C_1$–$C_4$-alkoximino, phenyl or phenoxy, each of which may, if desired, have from 1 to 5 halogen atoms on the aromatic moiety and the phenyl or naphthyl group may carry a number of halogen atoms, $C_1$–$C_4$-alkyl radicals, partially or completely halogenated $C_1$–$C_4$-alkyl radicals and/or $C_1$–$C_4$-alkoxy radicals such that the total number of radicals is 5; 5-membered or 6-membered hetaryl having a nitrogen, oxygen or sulfur atom and, if desired, up to 2 further nitrogen atoms as hetero atoms, with the exception of heterocyclic structures having 3 adjacent hetero atoms, where the heteroaromatic structure may furthermore carry up to 3 halogen atoms, $C_1$–$C_4$-alkyl radicals, partially or completely halogenated $C_1$–$C_4$-alkyl radicals or $C_1$–$C_4$-alkoxy radicals or up to 2 of the following radicals: cyano, nitro, $C_1$–$C_4$-alkoximino, phenyl or phenoxy, both of which may furthermore carry up to 5 halogen atoms on the aromatic moiety, and $R^2$ may additionally be hydrogen when X and Y together form a radical

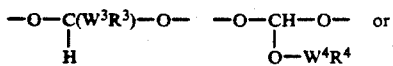

-continued
$$-O-\underset{\underset{O-W^4R^4}{|}}{C(W^3R^3)}-O-$$

and $W^2$ is a direct bond,
with the exception of cis-1-(2,4-dichlorophenyl)-2-(pyrid-3-yl)-1,2-epoxypropane, trans-1-(2,4-dichlorophenyl)-2-(pyrid-3-yl)-1,2-epoxypropane, 1-(2,4-dichlorophenyl)-2-(pyrid-3-yl)-1,2-epoxybutane and 2,4-dichloro-α-[1-hydroxy-1-(pyrid-3-yl)-ethyl]-benzyl methanesulfonate, and the N-oxides and the plant-tolerated mineral acid salts and metal complexes of I.

The present invention furthermore relates to processes for the preparation of these compounds, their use as fungicides and fungicides which contain these compounds as active substances.

Tetrahedron 24 (1968), 1959 discloses cis- and trans-1-phenyl-2-(pyrid-3-yl)-oxirane, for which, however, no biological action is indicated. Furthermore, this publication discloses pyridylethanediols of the formula II, e.g. 1-phenyl-2-(pyrid-3-yl)ethane-1,2-diol

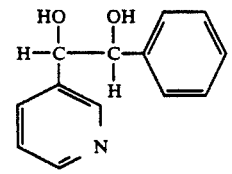

Moreover, EP-A 74 018 discloses fungicidal 3-substituted pyridines and pyridine N-oxides which are of the same type as the compounds I and in which X is hydroxyl, Y is hydrogen, halogen, alkyl, methylthio or methylsulfonyl or X and Y together are oxygen, $W^1$ and $W^2$ are each a direct bond, $R^1$ is 2,4-dichlorophenyl and $R^2$ is alkyl.

However, the fungicidal actions of these compounds are satisfactory only to a limited extent, particularly at low application rates and concentrations.

It is an object of the present invention to provide novel fungicidal substances.

We have found that this object is achieved by the 3-substituted pyridines of the formula I which are defined at the outset.

The variables in the novel compounds I have the following specific meanings:
X is hydroxyl,
Y is —O—CHO, —O—CO—$W^3R^3$ or —O—$SO_2$—$W^3R^3$ or
X and Y together are oxygen or

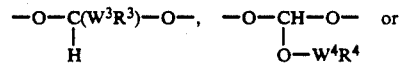

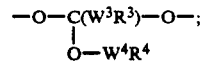

$W^1$, $W^2$, $W^3$ and $W^4$ are each a direct bond; —$CH_2$—, —$CH_2$—$CH_2$— or —$CH(CH_3)$—; —$CH_2$—O— or —$CH_2$—S—, where the bond to the radicals $R^1$ to $R^4$ is via the oxygen or sulfur atom;
$R^1$, $R^2$, $R^3$ and $R^4$ are each branched or straight-chain $C_1$–$C_6$-alkyl, in particular $C_1$–$C_4$-alkyl, such as methyl, ethyl, n-propyl, isopropyl, n-butyl, 1- methylprop-1-yl or tert-butyl, which may carry a C$_3$-C$_8$-alkyl radical, in particular a cyclopropyl, cyclopentyl or cyclohexyl radical, for example cyclopropylmethyl, 1-cyclopropylethyl, 2-cyclopropylethyl, cyclopentylmethyl, 1-cyclopentylethyl or 1-cyclohexylethyl; isopropyl is particularly preferred;

branched or straight-chain, partially or completely halogenated C$_1$-C$_6$-alkyl, in particular C$_1$-C$_4$-alkyl, such as fluoromethyl, chloromethyl, bromomethyl, difluoromethyl, trifluoromethyl, trichloromethyl, 1-chloroethyl, pentafluoroethyl, 4-chlorobut-1-yl or 2-chloro-1,1,2-trifluoroethyl, in particular trifluoromethyl;

C$_3$-C$_8$-cycloalkyl, such as cyclopropyl, cyclobutyl, cyclopentyl, cyclohexyl, cycloheptyl or cyclooctyl, in particular cyclopropyl, cyclopentyl or cyclohexyl, where the cycloalkyl group may furthermore carry from one to three branched or straight-chain C$_1$-C$_6$- alkyl substituents, in particular C$_1$-C$_4$-alkyl such as methyl, ethyl, n-propyl, isopropyl, n-butyl, 1-methylprop-1-yl tert-butyl, or preferably 1-methylcyclopropyl, 2-methylcyclopropyl, 3-isopropylcyclohexyl, 4-tert-butylcyclohex-1-yl or 2-isopropyl-5-methylcyclohex-1-yl;

C$_1$-C$_4$-alkoxy-C$_1$-C$_4$-alkyl or C$_1$-C$_4$-alkylthio-C$_1$-C$_4$-alkyl, such as methoxymethyl, ethoxymethyl, 1-methoxyeth-1-yl, 2-ethoxyethyl, 2-butoxyethyl, tert-butoxymethyl, methylthiomethyl, ethylthiomethyl, tert-butylthiomethyl or methylthioethyl;

C$_2$-C$_6$-alkenyl, such as vinyl, allyl, 2-methylallyl, 3-methylallyl, prop-2-en-2-yl, 3,3-dimethylallyl or 3-buten-1-yl, particularly preferably vinyl;

C$_2$-C$_6$-alkynyl, in particular C$_2$-C$_4$-alkynyl, such as ethynyl, propargyl, but-1-yn-1-yl or prop-1-yn-1-yl;

phenyl or naphthyl, where these groups may furthermore carry a total of from one to five radicals, in particular
one or two nitro groups,
one or two cyano groups,
one or two C$_1$-C$_4$-alkoximino groups, in particular methoximino or ethoximino,
one or two phenyl and/or phenoxy groups, both of which may furthermore carry up to 5 halogen atoms, such as fluorine, chlorine, bromine or iodine, preferably fluorine or chlorine;
up to 5 halogen atoms, such as fluorine, chlorine, bromine or iodine, preferably fluorine, chlorine or bromine,
up to 5 C$_1$-C$_4$-alkyl groups, such as methyl, ethyl, n-propyl, isopropyl, n-butyl, 1-methylprop-1-yl or tertbutyl,
up to 5 partially or completely halogenated C$_1$-C$_4$-alkyl groups, such as fluoromethyl, chloromethyl, bromomethyl, difluoromethyl, trifluoromethyl, trichloromethyl, 1-chloroethyl, pentafluoroethyl, 4-chlorobut-1-yl or 2-chloro-1,1,2-trifluoroethyl, preferably trifluoromethyl, or
up to 5 C$_1$-C$_4$-alkoxy groups, such as methoxy, ethoxy, n-propoxy, isopropoxy, n-butoxy or tertbutoxy;
particlarly preferably phenyl, 2-nitrophenyl, 4-nitrophenyl, 2-cyanophenyl, 4-cyanophenyl, 2-cyano-4-chlorophenyl, biphenyl, 4-phenoxyphenyl, 4-(4'-chlorophenoxy)phenyl, C$_1$-C$_4$-alkoximinophenyl, such as 4-methoximinophenyl or 4-ethoximinophenyl, halophenyl, such as 2-fluorophenyl, 4-fluorophenyl, 2-chlorophenyl, 4-chlorophenyl, 2-bromophenyl, 4-bromophenyl, 2-chloro-4-nitrophenyl, 2-chloro-4-cyanophenyl, 2-chloro-4-methylphenyl or 2-bromo-4-methylphenyl, dihalophenyl, such as 2,3-dichlorophenyl, 2,4-dichlorophenyl, 2,6-dichlorophenyl, 2-chloro-3-fluorophenyl,2-chloro-4-fluorophenyl, 2-bromo-4-fluorophenyl or 2-bromo-4-chlorophenyl, C$_1$-C$_4$-alkylphenyl, such as 2-methylphenyl, 4-methylphenyl or 4-tert-butylphenyl, C$_1$-C$_4$-haloalkylphenyl, such as 2-trifluoromethylphenyl or 4-trifluoromethylphenyl, and C$_1$-C$_4$-alkoxyphenyl, such as 2-methoxyphenyl, 4-methoxyphenyl or 4-tert-butoxyphenyl; 4-fluorobenzyl and 2,4-dichlorobenzyl are very particularly preferred;

a 5-membered or 6-membered hetaryl group having a nitrogen, oxygen or sulfur atom and, if desired, additionally 1 or 2 nitrogen atoms as hetero atoms, with the exception of heterocyclic structures having 3 adjacent hetero atoms in the cyclic moiety, for example pyrrol-2-yl, thien-2-yl, furan-2-yl, isoxazol-5-yl, pyrazolyl, 1,3,4-triazol-2-yl, pyrid-2-yl, pyrid-3-yl, pyrid-4-yl and pyrimidyl, where these groups may furthermore carry on the carbon atoms up to 3 halogen atoms as stated above, in particular fluorine, chlorine or bromine, C$_1$-C$_4$-alkyl groups as stated above, in particular methyl, isopropyl or tertbutyl, and/or C$_1$-C$_4$-alkoxy groups as stated above, in particular methoxy or ethoxy, or up to 2 of the following radicals: nitro, cyano, C$_1$-C$_4$-alkoximino, in particular methoximino or ethoximino, or phenyl or phenoxy, both of which may furthermore carry up to 5 halogen atoms, such as fluorine, chlorine, bromine or iodine, in particular fluorine or chlorine, for example 2-chlorothien-3-yl, 3-bromothien-2-yl, 3-isopropylisoxazol-5-yl or 3-phenylisoxazol-5-yl; and R$^2$ may additionally be hydrogen when X and Y together form a radical

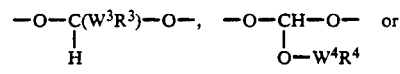

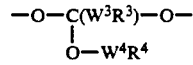

and W$^2$ is a direct bond.

Particularly preferred substituents I are shown in the Tables of the Examples.

1-Acetoxy-1-(2,4-dichlorophenyl)-2-(pyrid-3-yl)-3-methylbutan-2-ol, 1-(2,4-dichlorophenyl)-1-methylsulfonyloxy-2-(pyrid-3-yl)-hexan-2-ol, 1-isopropyl-1-(pyrid-3-yl)-2-(2,4-dichlorophenyl)-oxirane, 2-methoxy-2-methyl-4-(pyrid-3-yl)-4-isopropyl-5-(2,4-dichlorophenyl)-1,3-dioxolane, 2-methoxy-2-methyl-4-(pyrid-3-yl)-4-vinyl-5-(2,4-dichlorophenyl)-1,3-dioxolane, 2-methoxy-2-methyl-4-(4-fluorophenyl)-4-(pyrid-3-yl)-5-(2,4-dichlorophenyl)-1,3-dioxolane, 2-(4-methylphenyl)-4-(pyrid-3-yl)-5-(2-bromophenyl)-1,3-dioxolane, 2-phenyl-4-(pyrid-3-yl)-5-(2,4-dichlorophenyl)-1,3-dioxolane, 2-phenyl-4-(pyrid-3-yl)-5-(2-chlorophenyl)-1,3-dioxolane and 2-(4-methylphenyl)-4-(pyrid-3-yl)-5-(2-chlorophenyl)-1,3-dioxolane are very particularly preferred.

The 3-substituted pyridines are obtainable in various ways, preferably by the following methods:

a) Preparation of compounds I in which X is hydroxyl and Y is —O—CHO, —O—CO—W³R³ or —O—SO₂—W³R³:

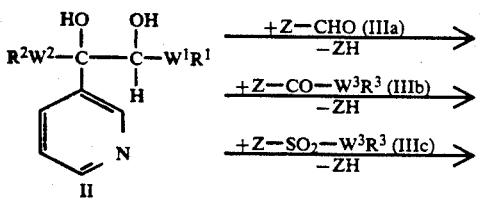

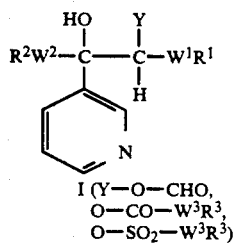

I (Y=O—CHO,
O—CO—W³R³,
O—SO₂—W³R³)

Z is halogen, in particular chlorine or bromine, acyloxy or sulfonyloxy.

The reaction is advantageously carried out in a solvent or diluent at atmospheric pressure, particularly preferably with the addition of an organic or inorganic base. Reduced or superatmospheric pressure is possible but generally has no advantages.

Suitable solvents or diluents are aliphatic hydrocarbons, such as n-pentane, n-hexane or cyclohexane, aromatic hydrocarbons, such as toluene or o-, m- or p-xylene, chlorohydrocarbons, such as methylene chloride, chloroform or carbon tetrachloride, ethers, such as diethyl ether or tetrahydrofuran, and esters, such as ethyl acetate.

Examples of suitable bases are alkali metal hydroxide, in particular sodium hydroxide or potassium hydroxide, alkali metal carbonates, such as sodium carbonate or potassium carbonate, bicarbonates, such as sodium bicarbonate or potassium bicarbonate, and amines, such as triethylamine, pyridine or 4-dimethylaminopyridine, in not less than the stoichiometric amount, based on the amount of II, for complete conversion.

The compounds II may also be first converted into the corresponding alcoholates in a separate process step by means of a base.

If Z is acyloxy or sulfonyloxy, it is advisable to use tertiary amines, such as triethylamine or pyridine, as the base, the reaction particularly preferably being carried out in the absence of a solvent and in an excess of the base.

By adding a catalyst, preferably 4-dimethylaminopyridine, it may be possible to increase the reaction rate [cf. Angew. Chemie 90 (1978), 602].

All starting compounds are usually used in a roughly stoichiometric ratio, but an excess of one or other component, for example up to 10%, may be advisable in some cases.

If an organic base is simultaneously used as the solvent, it is present in a relatively large excess.

In general, the reaction temperature is from 0 to 100° C., in particular the reflux temperature of the relevant solvent.

The pyridylethanediols II are disclosed in, for example, the following publications: JP-A 48/5593, Tetrahedron 24 (1968), 1959, J. Org. Chem. 52 (1987), 957, Helv. Chem. Acta 68 (1985), 600, Chem. Heterocycl. Compounds 10 (1974), 210, Acta Pharm. Succ. 9 (4) (1972), 289 and EP-A 209 854. Further derivatives II can be prepared by the methods stated in the above publications or by the processes described in German Patent Application P 3943277.

The starting compounds IIIa to IIIc are known or can be prepared by known processes.

b) Preparation of compounds I in which X and Y together are an oxygen atom, by reacting a 3-substituted pyridine Ia with a base:

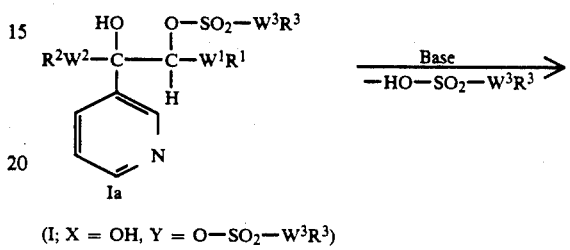

(I; X = OH, Y = O—SO₂—W³R³)

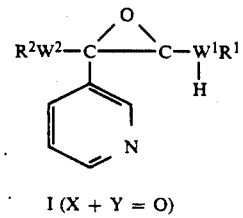

I (X + Y = O)

The reaction is advantageously carried out in an inert solvent or diluent at atmospheric pressure, the reaction temperature generally being from 20° C. to the reflux temperature of the particular solvent.

The reaction is usually carried out in an inert solvent or diluent by a conventional process, suitable bases being, for example, alkali metal hydroxides, such as potassium hydroxide [cf. Furst, Helv. 32 (1954), 1454], alkali metal alkoxides, such as sodium methoxide [cf. Reist, J. Org. Chem. 30 (1965), 3401], tetraalkylammonium hydroxides, such as triethylammonium hydroxide [cf. Marshall, THL 27 (1986), 5197] and tertiary amines, such as triethylamine [cf. Ogate, J. Med. Chem. 30 (1987), 1054].

Regarding the solvents, the pressure, the temperature and the ratios, the data for method (a) are applicable.

In a very particularly preferred embodiment, the 3-substituted pyridines I (where X+Y together are oxygen) are prepared in a 1-stage synthesis directly from the pyridylethanediols II by reacting the latter with compounds IIIa, IIIb or IIIc in the presence of an excess amount of a base. A particularly suitable base is triethylamine. The reaction is advantageously carried out in an inert diluent, in particular in methylene chloride.

The ratios are not critical. The educts II and IIIa, IIIb or IIIc are usually used in a stoichiometric ratio, but an excess of the compounds IIIa, IIIb or IIIc, for example up to 50%, may also be advantageous.

In general, the reaction is carried out at atmospheric pressure or at the autogenous pressure of the particular solvent, a reaction temperature of from 20° C. to the boiling point of the solvent being advisable.

c) Preparation of compounds I in which X and Y together form a group

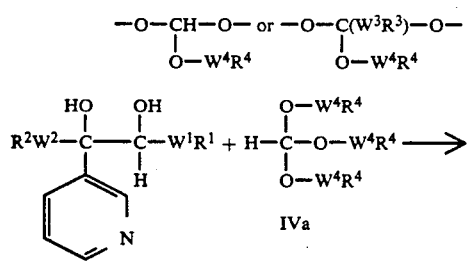

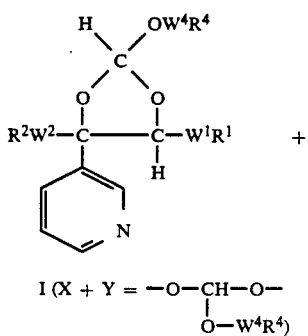

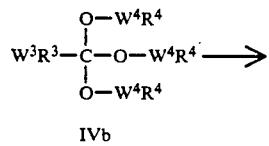

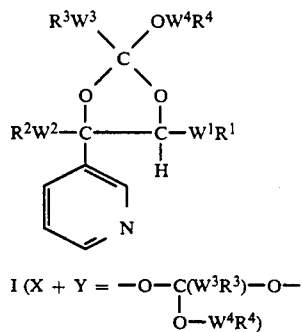

The reaction is advantageously carried out in an inert solvent or diluent, for example in a hydrocarbon, such as toluene, o-, m- or p-xylene, or in a halohydrocarbon, such as methylene chloride, chloroform or 1,2-dichloroethane, or in an excess of the orthoester IVa or IVb.

It is particularly advantageous if the reaction is effected in the presence of a strong acid, such as hydrochloric acid, sulfuric acid or para-toluenesulfonic acid, the amount of acid not being critical.

An excess of the orthoester IVa or IVb of up to 30 mol %, based on the amount of pyridylethanediol II is usually used, but in some cases it may be advisable to carry out the reaction in the absence of a solvent, in a relatively large excess of orthoester.

In general, the reaction is carried out at from 20° to 120° C., preferably at the boiling point of the solvent used.

Advantageously, atmospheric pressure or the autogenous pressure of the particular solvent is employed. In a particularly preferred version of the process, the pyridylethanediols II are reacted with trimethyl or triethyl orthoacetate to give compounds I in which W is a direct bond and $R^4$ is methyl or ethyl. These products can then be converted into further 3-substituted pyridines I in a further process step by reaction with alcohols $R^4W^4$-OH in the presence of an acid [cf. de Wolfe, Synthesis, 165 (1974)]:

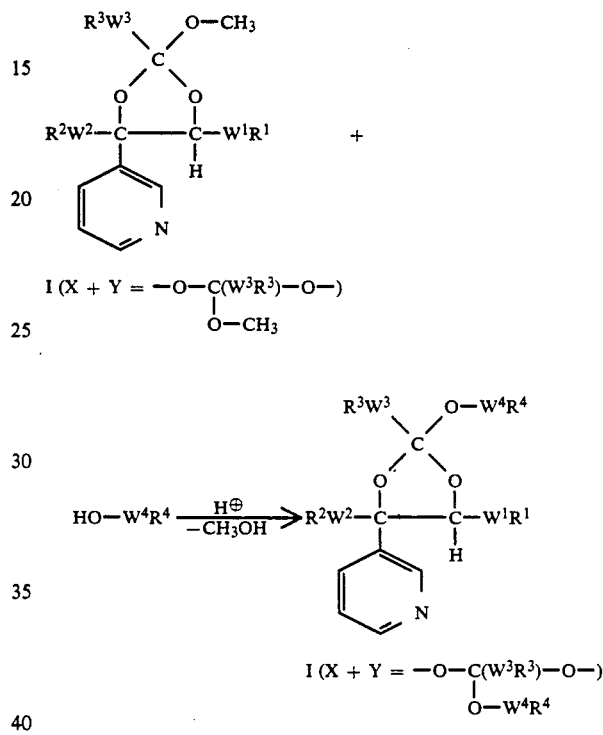

This reaction is preferably carried out in the absence of a solvent, in an excess of the particular alcohol HO-$W^4R^4$, the methanol advantageously being distilled off from the reaction mixture at the rate at which it is formed.

d) Preparation of compounds I in which X and Y together form a group

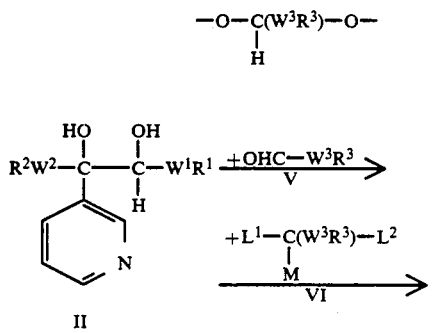

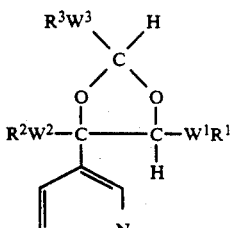

I (X + Y = —O—C(W³R³)—O—).

$L^1$ and $L^2$ are each halogen, preferably chlorine or bromine, or $C_1$-$C_4$-alkoxy, preferably methoxy or ethoxy.

Acetalization reactions with compounds of the formula V are generally known reactions of organic chemistry. They are usually carried out in the presence of a strong acid (Organikum, page 490, 15th edition), 1977 or a Lewis acid (R. Masuda, Tetrahedron Lett. 26 (1977), 4767) in order to accelerate the reaction. In a preferred embodiment, for example, both reactants are refluxed together with an azeotrope-forming solvent in the presence of a strong acid, such as p-toluenesulfonic acid. Examples of suitable solvents are chloroform, carbon tetrachloride, chlorobenzene, aromatic hydrocarbons, such as benzene, toluene or xylene, and mixtures thereof.

Where $L^1$ and $L^2$ are each alkoxy, such as methoxy or ethoxy, reactions with compounds of the formula VI correspond to a transacetalization reaction. These are usually likewise carried out with the addition of a strong acid (J. March, Adv. Org. Chem. page 345, 3rd edition, 1985). Another conventional method for the preparation of cyclic acetals comprises using geminal dihalides, in particular chlorides and/or bromides, in the presence of nitrogen bases, such as pyridine, for the cyclization reaction (P. J. Garegg et al., Acta Chem. Scand. 26 (1972), 518 et seq. and 3895 et seq.).

The reaction of pyridylethanediols II with an excess of a dimethylacetal VI (where $L^1$ and $L^2$ are each $OCH_3$) or of a diethylacetal IV (where $L^1$ and $L^2$ are each $OC_2H_5$) in the presence of a strong acid, such as sulfuric acid or p-toluenesulfonic acid, with or without the addition of a solvent, is particularly preferred, and the temperature may increase to the boiling point of the reaction solution. Examples of suitable solvents are chloroform, carbon tetrachloride, chlorobenzene, aromatic hydrocarbons, such as benzene, toluene or xylene, and mixtures thereof.

Pyridylethanediols of the formula II in which $R^2$ is hydrogen and $W^2$ is a direct bond are obtained by reducing an acyloin of the formula VIIa or VIIb

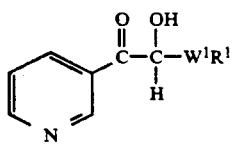

VIIa

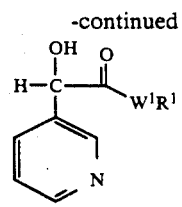

VIIb in which $R^1$ and $W^1$ have the abovementioned meanings. Suitable reducing agents are metal hydrides or hydrogen in the presence of a catalyst (cf. for example M. Hudlicky, Reductions in Org. Chem., page 119 et seq., 1984). Examples of suitable metal hydrides are diisobutylaluminum hydride and lithium, sodium, potassium and zinc borohydride or cyanoborohydride, as well as lithium aluminum hydrides of the general formula $LiAl(H)_m(OR)_n$, where m is from 1 to 4 and n is 4-m and R is alkyl, such as methyl, ethyl, propyl, isopropyl, n-butyl, isobutyl, tert-butyl or cyclohexyl. Sodium borohydride is very particularly preferred.

The reaction is generally carried out at from $-50°$ to $80°$ C., particularly preferably from $-20°$ to $50°$ C., very particularly from $-10°$ to $30°$ C. Suitable solvents are alcohols, such as methanol, ethanol, isopropanol or tertbutanol, and ethers, such as diethyl ether, methyl tertbutyl ether, tetrahydrofuran or dimethoxyethane.

Pyridylethanediols of the formula II in which $R^1$, $R^2$, $W^1$ and $W^2$ have the abovementioned meanings, with the exception that $R^2$ is not hydrogen, are obtained by subjecting an organometallic compound of the formula VIII to an addition reaction with an acyloin of the formula VIIa.

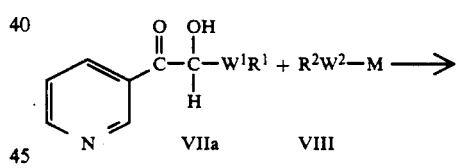

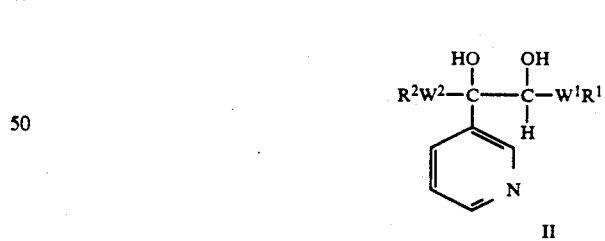

In formula VIII, $R^2$ and $W^2$ have the abovementioned meanings, with the exception that $R^2$ is not hydrogen. M is lithium or MgCl or MgBr.

The reaction is advantageously carried out by a method in which from 2 to 4 equivalents of the organometallic compound in an inert solvent, preferably diethyl ether, methyl tert-butyl ether, tetrahydrofuran or a mixture thereof, are initially taken and an acyloin of the formula VIIa is metered in at from $-30°$ to $50°$ C. In this reaction, it is also possible, instead of the acyloins VIIa, to use derivatives of the formula VIIa'

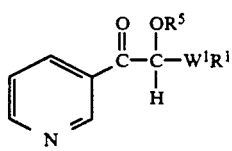

VIIa' where $W^1$ and $R^1$ have the abovementioned meanings and $R^5$ is a protective group of the OH function (T. W. Greene, Protective Groups in Org. Synth., pages 10–113, 1981), which can be eliminated after the reaction. Esters, such as acetate and benzoate, and ethers, such as methoxymethyl and trimethylsilyl ether, are preferred.

Pyridylethanediols of the formula II in which $R^1$ is hydrogen, $W^1$ is a direct bond and $R^2$ and $W^2$ have the abovementioned meanings can be prepared by reacting a 3-pyridyl ketone of the formula IX with dimethylsulfonium or diethylsulfoxonium methylide:

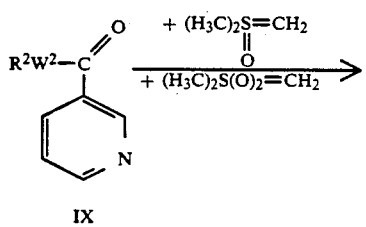

3-Pyridyl ketones of the formula IX are generally known compounds which can be prepared by a large number of known methods. In a preferred method, for example, alpha-morpholino-3-pyridylacetonitrile is alkylated and the ketone function is then liberated (E. Leete et al., JOC-37 (1972), 4465) or 3-pyridyllithium (Wibaut et al., Rec. Trav. chim. 77 (1958), 1057) is subjected to an additon reaction with a correspondingly substituted nitrile and the mixture is then worked up under acidic conditions. The formation of oxiranes X by reacting 3-pyridyl ketones with dimethylsulfonium or dimethylsulfoxonium methylide is known (M. Sainsbury et al., JCS Perk. Trans. 1 (1982), 587 et seq.). The opening of the epoxides X to give the pyridylethanediols II is achieved by the addition of an acid or base (J. March, Adv. Org. Chem. 3rd Ed., page 332, 1985).

Pyridylethanediols of the general formula II'

II' where $R^1$, $R^2$, $W^1$ and $W^2$ have the abovementioned meanings, with the proviso that $R^1W^1$ is not hydrogen, vinyl, unsubstituted phenyl or 3-pyridyl when $R^2W^2$ is hydrogen and with the proviso that $R^1W^1$ is not 2,4-dichlorophenyl when $R^2W^2$ is methyl and with the proviso that $R^2W^2$ is not unsubstituted phenyl or 4-methoxyphenyl when $R^1W^1$ is unsubstituted phenyl and with the proviso that $W^2$ is not —$CH_2$— or —CH(CH$_3$)— when $R^1$ is hydrogen or $C_1$-$C_5$-alkyl, $R^2$ is unsubstituted or substituted phenyl and $W^1$ is a direct bond, are novel.

The acyloins of the formula VIIa and VIIb are also novel. Acyloins of the formula VIIa can be prepared, for example, by subjecting 3-pyridylmagnesium bromide or chloride to an addition reaction with O-trimethylsilylcyanohydrins (J. K. Rasmussen et al., THL 24 (1983), 4075 et seq.). However, the acyloin condensation of 3-pyridylaldehyde with aldehydes of the formula XI where $R^1$ and $W^1$ have the abovementioned meanings, is preferred. The reaction can be catalyzed by cyanide ions (P. Bergmann and H. Paul, Z. Chem. page 339 et seq., 1966) or by thiazolium salts (A. Stetter et al., Synthesis, page 733, 1976). Thiazolium salt-catalyzed acyloin condensations with 3-pyridinealdehyde were previously unknown. It is therefore to be regarded as very surprising that in many cases very high yields of the mixed acyloins VIIa and VIIb are obtained and the symmetric acyloins of the formulae XIIa and XIIb are obtained only as byproducts, if at all:

Of the two acyloins VIIa and VIIb, the acyloin VIIa is often obtained in excess.

The N-oxides of the 3-substituted pyridines I can be prepared by conventional methods from the compounds I, for example by reacting them with an organic peracid, such as metachloroperbenzoic acid.

Suitable addition salts with acids are the addition salts of acids which do not adversely affect the fungicidal action of I, for example the salts of hydrochloric acid, hydrobromic acid, sulfuric acid, nitric acid, phosphoric acid, boric acid, formic acid, acetic acid, propionic acid, lauric acid, palmitic acid, stearic acid, oxalic acid, malic acid, malonic acid, benzoic acid, methanesulfonic acid, benzenesulfonic acid, toluenesulfonic acid, dodecylbenzenesulfonic acid and saccharic acid.

Suitable metal complexes ar the complexes of copper, of zinc, of tin, of manganese, of iron, of cobalt or of nickel. The complexes are preferably prepared from the free bases I and salts of the metals with mineral acids, for example the chlorides or sulfates.

The novel compounds I can occur in a plurality of isomeric forms, but in not less than 2 isomeric forms. In most preparation processes, mixtures of the possible isomers are obtained, in general racemates or diastereomer mixtures, which, however, can be separated, if desired, into the pure isomers by conventional methods, for example by chromatography over an optically active adsorbent.

The 3-substituted pyridines I are suitable as fungicides, both in the form of racemates or diastereomer mixtures and in the form of the pure isomers.

The 3-substituted pyridines I have excellent activity against a broad spectrum of phytopathogenic fungi, in particular from the class consisting of the Ascomycetes and Basidiomycetes. Some of them are systemically active and may be used as leaf and fungicides soil.

It may also be useful to apply the 3-substituted pyridines I, alone or in combination with other herbicides, as a mixture together with further crop protection agents, for example with pesticides, agents for controlling phytopathogenic fungi or bactericides. The miscibility with mineral salt solutions, which are used for eliminating nutrient and trace element deficiencies, is also of interest. Nonphytotoxic oils and oil concentrates may also be added.

PREPARATION EXAMPLES

Example 1

1-(pyrid-3-yl)-2-(2-bromophenyl)-ethanediol

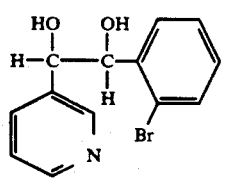

20 g (0.068 mol) of 1-(pyrid-3-yl)-2-(2-bromophenyl)-2-hydroxyethanone in 300 ml of methanol were reduced with 3 g (0.079 mol) of sodium borohydride at 0° C. Stirring was carried out for a few hours at room temperature (21° C.), the pH was brought to 2 with 4N hydrochloric acid and 4 ml of ethylene glycol were added. The solution was evaporated down, after which the residue was covered with a layer of ethyl acetate and neutralized with NaHCO$_3$ solution. The ethyl acetate phase was washed twice with water and dried over Na$_2$SO$_4$. After the ethyl acetate had been distilled off, the product was obtained as a white powder of melting point 115° C.

Intermediate 1.1

1-(Pyrid-3-yl)-2-(2-bromophenyl)-2-hydroxyethanone 146 g (0.8 mol) of 2-bromobenzaldehyde, 85.6 g (0.8 mol) of 3-pyridinealdehyde, 20 g (0.08 mol) of 3-ethyl-5-(2-hydroxyethyl)-4-methylthiazoliumbromide and 40.4 g (0.4 mol) of triethylamine in 500 ml of ethanol were heated at 75° C. for 16 hours. Thereafter, the ethanol was distilled off and the residue was taken up in methylene chloride. The solution was washed twice with water and then extracted twice with 300 ml of 4N hydrochloric acid. The acidic aqueous phase was then rendered slightly alkaline with 4N sodium hydroxide solution and extracted three times with methylene chloride. After the solvent had been distilled off, the crude product was stirred with isopropanol, filtered off under suction and dried to give a product of melting point 105°–108° C.

Example 2

3-(Pyrid-3-yl)-4-(2-chlorophenyl)-but-1-ene-3,4-diol

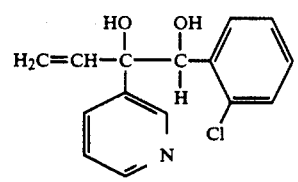

A solution of 13 g (0.0531 mol) of 1-(pyrid-3-yl)-2-(2-chlorophenyl)-2-hydroxyethanone in tetrahydrofuran (THF) was added dropwise to a freshly prepared solution of 0.18 mol of vinylmagnesium bromide in 80 ml of THF at room temperature. Stirring was carried out for three hours at room temperature, after which the solution was hydrolyzed by adding ammonium chloride solution. The aqueous phase was extracted twice with ethyl acetate. The collected organic phases were dried over Na$_2$SO$_4$ and then filtered, and the filtrate was evaporated down. The crude product was stirred with methyl tert-butyl ether, filtered off under suction and dried to give a product of melting point 110°–112° C.

Intermediate 2.1

1-(Pyrid-3-yl)-2-(2-chlorophenyl)-2-hydroxyethanone 160 g (1.14 mol) of 2-chlorobenzaldehyde, 122 g (1.14 mol) of 3-pyridinealdehyde, 50 g (0.2 mol) of 3-ethyl-5-(2-hydroxyethyl)-4-methylthiazoliumbromide and 60.6 g (0.6 mol) of triethylamine in one liter of ethanol were heated at 75° C. for 13 hours. Thereafter, the ethanol was distilled off and the residue was dissolved in methylene chloride. The solution was washed twice with water and then extracted twice with 300 ml of 4N hydrochloric acid. The acidic aqueous phase was then rendered slightly alkaline with 4N sodium hydroxide solution and extracted three times with fresh methylene chloride. After the solvent had been distilled off, the crude product was stirred with isopropanol, filtered off under suction and dried to give a product of melting point 92° C.

Example 3

2-(Pyrid-3-yl)-4-methylbutane-1,2-diol

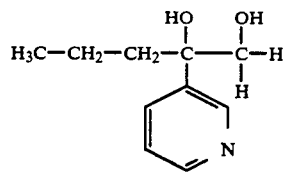

20 g (0.134 mol) of 3-pyridyl isopropyl ketone and 30.2 g (0.268 mol) of potassium tert-butylate were dissolved in 200 ml of tert-butanol. Thereafter, 37.4 g (0.208 mol) of trimethylsulfonium iodide were added and the mixture was heated at 65° C. for 1.5 hours. The inorganic salts were separated off and the reaction solution was evaporated down, after which 75 ml of half-concentrated $H_2SO_4$ were added to the crude product and the mixture was heated at 60°-70° C. for 8 hours. The pH was then brought to 9 with 4N NaOH solution and extraction was carried out with methylene chloride. The organic phase was dried and evaporated down and the product was then purified by chromatography.

$^1$H-NMR (CDCl$_3$/TMS$_{int}$): δ/ppm=0.75 (d, 3H), 0.82 (d, 3H), 2.07 (sept, 1H), 3.4 (s, broad, 1H), 3.85 (d, 1H), 4.08 (d, 1H), 7.1 (m, 1H), 7.8 (m, 1H), 8.35 (m, 1H), 8.52 (d, 1H)

IR: /cm$^{-1}$=3309, 3108, 2960, 1149, 1074, 1058, 908

Intermediate 3.1

Pyrid-3-yl isopropyl ketone 133 g (0.70 mol) of alpha-morpholino-3-pyridylacetonitrile, 25.7 g (0.07 mol) of tetrabutylammonium iodide, 278 g (3.5 mol) of 50% strength NaOH, 250 ml (2.65 mol) of isopropyl bromide and 300 ml of toluene, as a two-phase system, were heated at 50° C. for 4 hours with thorough mixing. Working up was carried out by adding water, separating the phases and washing the organic phase three times with water. After the solvent had been distilled off, the crude product in the form of an oil was added dropwise to half-concentrated $H_2SO_4$ at 60° C. After 2 hours, the mixture was brought to pH 9 with 50% strength NaOH and was extracted with toluene. The organic phase was washed three times with water and the wash solution was extracted 4 times with toluene. The collected toluene extracts were dried over $Na_2SO_4$ and filtered and the filtrate was evaporated down. The product was obtained as a dark oil.

$^1$H-NMR (CDCl$_3$/TMS$_{int}$): δ/ppm=1.25 (d, 6H), 3.55 (sept, 1H), 7.45 (m, 1H), 8.25 (m, 1H), 8.8 (m, 1H), 9.2 (d, 1H)

Example 4

1-Acetoxy-1-(2,4-dichlorophenyl)-2-(pyrid-3-yl)-3-methylbutan-2-ol (Compound No. 1.01)

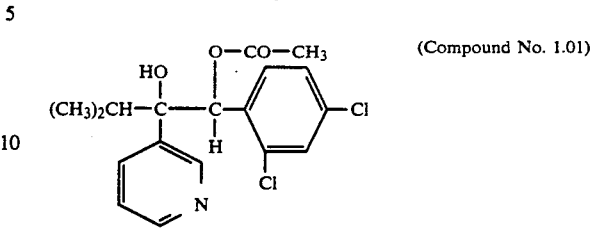

38.2 ml (0.4 mol) of acetic anhydride were added dropwise to a solution of 76 g (0.23 mol) of 1-(2,4-dichlorophenyl)-2-(3-pyridyl)-3-methylbutane-1,2-diol, 197.7 ml (1.318 mol) of triethylamine and about 0.5 g (4 mmol) of 4-N,N-dimethylaminopyridine in 1 l of methylene chloride while heating at 35° C. After cooling to room temperature, the mixture was stirred for a further 30 minutes and then poured into 500 ml of a saturated sodium bicarbonate solution. The organic phase was separated off and was worked up in a conventional manner to obtain the product. The oily crude product was crystallized by stirring with ethyl acetate. Yield: 56%.

Example 5

1-(2,4-Dichlorophenyl)-1-methylsulfonyloxy-2-(pyrid-3-yl)-octan-2-ol (Compound No. 2.04)

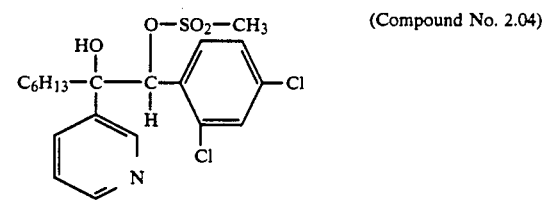

23.6 ml (177 mmol) of triethylamine were added dropwise to a mixture of 8.5 g (23 mmol) of 1-(2,4-dichlorophenyl)-2-(pyrid-3-yl)-octane-1,2-diol, 2.5 ml (32 mmol) of methanesulfonyl chloride and 100 ml of methylene chloride at about 20° C. Thereafter, the mixture was washed with 30 ml of saturated sodium bicarbonate solution and 30 ml of water and was worked up in a conventional manner to obtain the product. The crude product was purified by chromatography. Yield: 50.6%.

Example 6

1-(Pyrid-3-yl)-1-(4-fluorophenyl)-2-(2-chlorophenyl)oxirane (Compound No. 3.16)

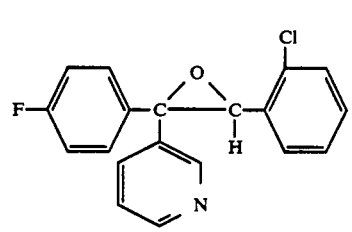

236 ml (1.77 mol) of triethylamine were added dropwise to a solution of 78.7 g (0.23 mol) of 1-(pyrid-3-yl)-

1-(4-fluorophenyl)-2-(2-chlorophenyl)-ethanediol and 25.2 ml (0.32 mol) of methanesulfonyl chloride 1 1 of methylene chloride at the reflux temperature. Stirring was carried out for a further 4 hours at the reflux temperature, after which the mixture was washed with 400 ml of saturated sodium bicarbonate solution and water and was then worked up in a conventional manner to obtain the product. The oily crude product was purified by flash chromatography using 8:3 cyclohexane/ethyl acetate as the mobile phase. 97% of a yellow oil were obtained.

Example 7

2-Methoxy-2-methyl-4-(pyrid-3-yl)-4-isopropyl-5-(2,4-dichlorophenyl)-1,3-dioxolane

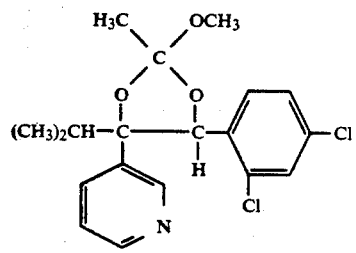

(Compound No. 4.01)

A solution of 6.7 g (21 mmol) of 1-(2,4-dichlorophenyl)-2-(pyrid-3-yl)-3-methylbutane-1,2-diol and about 0.3 g (1.7 mmol) of p-toluenesulfonic acid in 50 ml of methyl orthoacetate were stirred for 1 hour at 60° C. After excess methyl orthoacetate and the methanol formed had been slowly removed under reduced pressure, the residue was dissolved in 50 ml of methylene chloride. The organic phase was washed with saturated sodium bicarbonate solution and was worked up in a conventional manner to obtain the product. The crude product was purified by flash chromatography using 3:7 ethyl acetate/cyclohexane as the mobile phase. Yield: 49%.

Example 8

2-Phenyl-4-(pyrid-3-yl)-5-(2-bromophenyl)-1,3-dioxolane

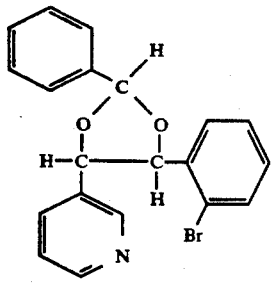

(Compound No. 5.69)

37 g (0.1258 mol) of 1-(pyrid-3-yl)-2-(2-bromophenyl)-ethanediol and 38.5 g (0.2516 mol) of benzaldehyde dimethyl acetal were refluxed together in 440 ml of 10:1 chlorobenzene/toluene with 1 g of p-toluenesulfonic acid. The resulting methanol was distilled off as an azeotrope with toluene. After the end of the reaction, the chlorobenzene was distilled off under reduced pressure and the product was purified by chromatography over silica gel.

Example 9

2-tert-Butyl-4-(pyrid-3-yl)-5-(2-bromophenyl)-1,3-dioxolane

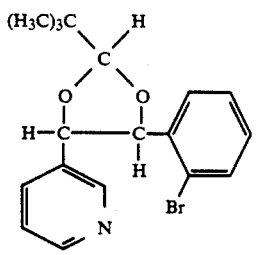

(Compound No. 5.70)

8 g (0.027 mol) of 1-(pyrid-3-yl)-2-(2-bromophenyl)-ethanediol and 4.5 g (0.0525 mol) of pivaldehyde were dissolved in 100 ml of methylene chloride. This was achieved by adding 4.35 ml (0.0525 mol) of boron trifluoride etherate dropwise at room temperature and stirring overnight. Thereafter, the mixture was poured onto ice water and was neutralized with NaHCO$_3$ solution. The organic phase was washed with water, dried over Na$_2$SO$_4$ and filtered, and the filtrate was evaporated down. The crude product was purified by chromatography.

$^1$H-NMR (CDCl$_3$/TMS$_{int}$): δ/ppm=1.2 (s, 9H), 4.85 (s, 1H), 5.5 (d, 1H), 5.7 (d, 1H), 6.9–7.5 (m, 6H), 8.25 (m, 1H), 8.5 (dm1H)

Example 10

2-Phenyl-4-(pyrid-3-yl)-4-ethenyl-5-(2-chlorophenyl)-1,3-dioxolane

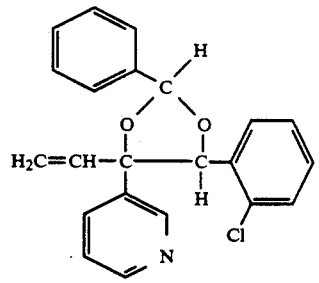

(Compound No. 5.71)

3 g (0.018 mol) of 3-(pyrid-3-yl)-4-(2-chlorophenyl)-but-1-ene-3,4-diol were dissolved in 50 ml of benzaldehyde dimethyl acetal. 1 ml of concentrated H$_2$SO$_4$ was then added and the mixture was heated to 80°–90° C. The excess benzaldehyde dimethyl acetal was distilled off under reduced pressure, together with the resulting methanol. The crude product was dissolved in methylene chloride and the solution was neutralized with NaHCO$_3$ solution. After the solvent had been separated off, the product was purified by chromatography.

The physical data of the end products I are shown in Tables 1 to 5 below, which also lists further compounds I which were, or can be, prepared by the same methods.

TABLE 1

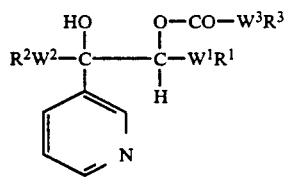

I (X = OH; Y = —O—CO—W³R³)

| No. | W¹R¹ | W²R² | W³R³ | Physical data mp. [°C.]; ¹H-NMR*) [ppm] |
|---|---|---|---|---|
| 1.01 | 2,4-dichlorophenyl | isopropyl | methyl | 162–167 |
| 1.02 | 2,4-dichlorophenyl | methyl | methyl | |
| 1.03 | 2,4-dichlorophenyl | isopropyl | ethyl | 110–112 |
| 1.04 | 2,4-dichlorophenyl | isopropyl | phenyl | 215–219 |
| 1.05 | 2,4-dichlorophenyl | isopropyl | n-propyl | 120–123 |
| 1.06 | 2,4-dichlorophenyl | isopropyl | 4-fluorobenzyl | |
| 1.07 | 2,4-dichlorophenyl | 4-fluorophenyl | methyl | |
| 1.08 | 2,4-dichlorophenyl | 4-fluorobenzyl | t-butyl | |
| 1.09 | 2,4-dichlorophenyl | isopropyl | hydrogen | |
| 1.10 | 2,4-dichlorophenyl | isopropyl | isopropyl | 140–143 |
| 1.11 | 2,4-dichlorophenyl | vinyl | methyl | |
| 1.12 | 2,4-dichlorophenyl | allyl | methyl | |
| 1.13 | 2-methoxyphenyl | phenyl | methylthiomethyl | |
| 1.14 | 3-chlorothien-3-yl | butyl | methyl | |
| 1.15 | 3-isopropylisoxazol-5-yl | 2,4-dichlorophenyl | 4-chlorophenyl | |

*) in CDCl₃, TMS as internal standard

TABLE 2

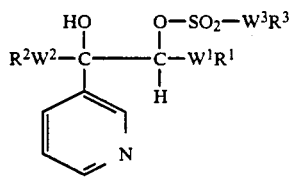

I (X = OH; Y = —O—SO₂—W³R³)

| No. | W¹R¹ | W²R² | W³R³ | Physical data mp. [°C.]; ¹H-NMR*) [ppm] |
|---|---|---|---|---|
| 2.01 | 2,4-dichlorophenyl | isopropyl | methyl | 138–140 |
| 2.02 | 2,4-dichlorophenyl | methyl | methyl | 155–160 |
| 2.03 | 2,4-dichlorophenyl | n-butyl | methyl | oil, NMR: 0.87 (t, 3H), 2.72 (s, 3H), 6.1 (s, 1H) |
| 2.04 | 2,4-dichlorophenyl | n-hexyl | methyl | 60–67 |
| 2.05 | 2,4-dichlorophenyl | isopropyl | phenyl | |
| 2.06 | 2,4-dichlorophenyl | isopropyl | 4-methylphenyl | |
| 2.07 | 2,4-dichlorophenyl | 4-fluorophenyl | methyl | |
| 2.08 | 2,4-dichlorophenyl | 4-fluorobenzyl | phenyl | |
| 2.09 | 2,4-dichlorophenyl | isopropyl | 4-chlorophenyl | |
| 2.10 | 2,4-dichlorophenyl | isopropyl | n-butyl | |
| 2.11 | 2,4-dichlorophenyl | vinyl | methyl | |
| 2.12 | 2,4-dichlorophenyl | allyl | methyl | |
| 2.13 | 2-methoxyphenyl | phenyl | 4-methylphenyl | |
| 2.14 | 3-chlorothien-3-yl | butyl | methyl | |
| 2.15 | 3-isopropylisoxazol-5-yl | 2,4-dichlorophenyl | 4-chlorophenyl | |
| 2.16 | 2,4-dichlorophenyl | 4-chlorophenethyl | methyl | 113–115 |
| 2.17 | 2,4-dichlorophenyl | 4-fluorophenethyl | methyl | 67–70 |

*) in CDCl₃, TMS as internal standard

TABLE 3

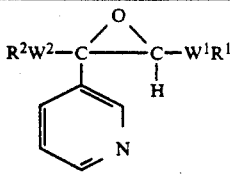

I  (X + Y = oxygen)

| No. | $W^1R^1$ | $W^2R^2$ | Physical data mp. [°C.]; $^1$H-NMR*) [ppm] |
|---|---|---|---|
| 3.01 | 2,4-dichlorophenyl | isopropyl | oil, NMR: 0.74 (d, 3H), 1.42 (m, 1H), 4.13 (s, 1H) |
| 3.02 | 2,4-dichlorophenyl | methyl | 92–103 |
| 3.03 | 2,4-dichlorophenyl | n-butyl | oil, NMR: 0.75 (t, 3H), 4.0 (2, 1H) |
| 3.04 | 2,4-dichlorophenyl | n-hexyl | oil, NMR: 0.8 (t, 3H), 4.0 (s, 1H) |
| 3.05 | 2,4-dichlorophenyl | benzyl | 140 |
| 3.06 | 2-bromophenyl | benzyl | 105–110 |
| 3.07 | 2-bromophenyl | 2-chlorobenzyl | 105–107 |
| 3.08 | 2-bromophenyl | 4-chlorobenzyl | 77 |
| 3.09 | 2,4-dichlorophenyl | 4-chlorobenzyl | 113 |
| 3.10 | 2,4-dichlorophenyl | 2-chlorobenzyl | 110–112 |
| 3.11 | 2,4-dichlorophenyl | 2,4-dichlorobenzyl | 126–128 |
| 3.12 | 2,4-dichlorophenyl | 4-fluorobenzyl | 122–124 |
| 3.13 | 2,4-dichlorophenyl | 4-fluorophenyl | 95–98 |
| 3.14 | 2,4-dichlorophenyl | 4-chlorophenethyl | oil, NMR: 1.6 (m, 1H), 2.18 (m, 1H), 2.35 (m, 2H), 4.02 (s, 1H) |
| 3.15 | 3-isopropylisoxazol-5-yl | 2,4-dichlorophenyl | |
| 3.16 | 2-chlorophenyl | 4-fluorophenyl | oil, NMR: 4.65 (s, 1H), 6.9 (t, 2H), 7.0–7.38 (m, 8H), 7.72–7.82 (m, 1H), 8.55–8.63 (m, 1H), 8.78 (d, 1H) |
| 3.17 | 2,4-dichlorophenyl | phenyl | |
| 3.18 | 2,4-dichlorophenyl | 4-chlorophenyl | 110–115 |
| 3.19 | 2,4-dichlorophenyl | 4-fluorophenethyl | oil, NMR: 2.35 (m, 2H), 4.03 (s, 1H) |
| 3.20 | 2,4-dichlorophenyl | vinyl | oil, NMR: 4.02 (s, 1H), 5.1–33 (m, 2H), 5.55–72 (m, 1H) |
| 3.21 | 2,4-dichlorophenyl | allyl | |
| 3.22 | 2-chlorothien-3-yl | isopropyl | |
| 3.23 | 2-methoxyphenyl | isopropyl | |

*)in CDCl$_3$, TMS as internal standard

TABLE 4

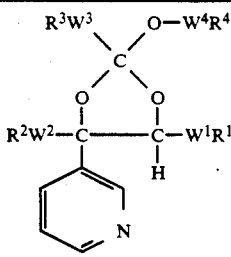

I  (X + Y = O—C($W^3R^3$)—O—)
              |
              O—$W^4R^4$

| No. | $W^1R^1$ | $W^2R^2$ | $W^3R^3$ | $W^4R^4$ | Physical data mp. [°C.]; $^1$H-NMR*) [ppm] |
|---|---|---|---|---|---|
| 4.01 | 2,4-dichlorophenyl | isopropyl | methyl | methyl | oil, NMR: 0.75 (d, 3H), 1.4 (d, 3H), 2,55 (m, 1H), 3.47 (s, 3H), 6.0 (s, 1H), 6.45–8.4 (m, 7H), 1.92 (s, 3H), 3.47 (s, 3H), 6.0 (s, 1H) |
| 4.02 | 2,4-dichlorophenyl | methyl | methyl | methyl | oil, NMR: 1.9 (s, 3H), 2.08 (s, 3H), 3.46 (s, 3H), 5.83 (s, 1H) |
| 4.03 | 2,4-dichlorophenyl | n-butyl | methyl | methyl | oil, NMR: 1.9 (s, 3H), 3.46 (s, 3H) 5.83 (s, 3H) |
| 4.04 | 2,4-dichlorophenyl | n-hexyl | methyl | methyl | oil, NMR: 1.9 (s, 3H), 3.48 (s, 3H) 5.93 (s, 1H) |
| 4.05 | 2,4-dichlorophenyl | isopropyl | phenyl | ethyl | |
| 4.06 | 2,4-dichlorophenyl | isopropyl | 4-methylphenyl | methyl | |
| 4.07 | 2,4-dichlorophenyl | 4-fluorophenyl | methyl | methyl | oil, NMR: 1.93 (s, 3H), 3.2 (s, 3H), 6.54 (s, 1H) |
| 4.08 | 2,4-dichlorophenyl | 4-fluorophenyl | methyl | methyl | oil, NMR: 1.92 (s, 3H), 3.52 (s, 3H), 5.95 (s, 3H) |
| 4.09 | 2,4-dichlorophenyl | isopropyl | 4-chlorophenyl | methyl | |
| 4.10 | 2,4-dichlorophenyl | isopropyl | n-butyl | methyl | |
| 4.11 | 2,4-dichlorophenyl | vinyl | methyl | methyl | 105–108 |
| 4.12 | 2,4-dichlorophenyl | allyl | methyl | methyl | |
| 4.13 | 2-methoxyphenyl | phenyl | 4-methylphenyl | methyl | |
| 4.14 | 2-chlorothien-3-yl | isopropyl | methyl | methyl | |
| 4.15 | 3-isopropyl-isoxazol-5-yl | 2,4-dichlorophenyl | 4-chlorophenyl | methyl | |
| 4.16 | 2,4-dichlorophenyl | benzyl | methyl | methyl | 155 |

TABLE 4-continued

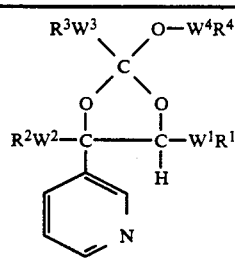

I (X + Y = O—C(W³R³)—O—)
                    |
                    O—W⁴R⁴

| No. | W¹R¹ | W²R² | W³R³ | W⁴R⁴ | Physical data mp. [°C.]; ¹H-NMR*) [ppm] |
|---|---|---|---|---|---|
| 4.17 | 2-bromophenyl | benzyl | methyl | methyl | 130–135 |
| 4.18 | 2-chlorophenyl | 4-fluorophenyl | methyl | methyl | oil, NMR: 1.93 (s, 3H), 3.2 (s, 3H), 6.6 (s, 1H) |
| 4.19 | 2-methoxyphenyl | 4-fluorophenyl | methyl | methyl | 117–124 |
| 4.20 | 2-fluorophenyl | 4-fluorophenyl | methyl | methyl | oil, NMR: 1.95 (s, 3H), 3.17 (s, 3H), 6.52 (s, 1H) |
| 4.21 | 2-methoxyphenyl | 4-fluorobenzyl | methyl | methyl | oil, NMR: 1.92 (s, 3H), 3.48 (s, 3H), 5.95 (s, 1H) |
| 4.22 | 2-chlorophenyl | 4-fluorobenzyl | methyl | methyl | oil, NMR: 1.92 (s, 3H), 3.53 (s, 3H), 6.05 (s, 1H) |
| 4.23 | 2-fluorophenyl | 4-fluorobenzyl | methyl | methyl | oil, NMR: 1.92 (s, 3H), 3.48 (s, 3H), 5.88 (s, 1H) |
| 4.24 | 2,4-dichlorophenyl | 2,4-dichlorobenzyl | hydrogen | methyl | 119–123 |
| 4.25 | 2,4-dichlorophenyl | phenyl | methyl | methyl | oil, NMR: 1.93 (s, 3H), 3.18 (s, 3H), 6.6 (s, 1H) |
| 4.26 | 2,4-dichlorophenyl | 4-chlorophenyl | methyl | methyl | oil, NMR: 1.93 (s, 3H), 3.2 (s, 3H), 6.53 (s, 1H) |
| 4.27 | 2,4-dichlorophenyl | 4-fluorophenethyl | methyl | methyl | oil, NMR: 1.96 (s, 3H), 3.5 (s, 3H), 5.88 (s, 1H) |
| 4.28 | 2,4-dichlorophenyl | 4-chlorobenzyl | methyl | methyl | 123–134 |
| 4.29 | 2,4-dichlorophenyl | 2-chlorobenzyl | methyl | methyl | oil, NMR: 1.96 (s, 3H), 3.48 (s, 3H), 6.0 (s, 1H) |
| 4.30 | 2,4-dichlorophenyl | 4-chlorophenethyl | methyl | methyl | oil, NMR: 1.93 (s, 3H), 3.47 (s, 3H), 5.88 (s, 1H) |

*)in CDCl₃, TMS as internal standard

TABLE 5

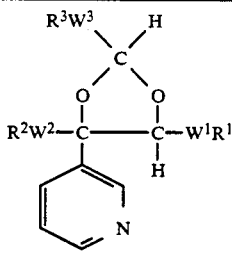

I (X + Y = —O—C(W³R³)—O—)
                    |
                    H

| No. | W¹R¹ | W²R² | W³R³ | Phys. data (mp. [°C.]; IR [cm⁻¹]; ¹H-NMR*) [ppm]) |
|---|---|---|---|---|
| 5.01 | 4-fluorophenyl | hydrogen | phenyl | oil, NMR: 6.2 (s, 1H), 5.58 (d, 1H) 5.52 (d, 1H) |
| 5.02 | 2-chlorophenyl | hydrogen | phenyl | oil, NMR: 6.2 (s, 1H), 5.9 (d, 1H), 5.72 (d, 1H) |
| 5.03 | 2,4-dichlorophenyl | hydrogen | phenyl | 93–95 |
| 5.04 | 2,4-dichlorophenyl | hydrogen | 4-methylphenyl | oil, NMR: 6.18 (s, 1H), 5.82 (d, 1H), 5.7 (d, 1H) |
| 5.05 | 2,4-dichlorophenyl | hydrogen | 4-fluorophenyl | 123–125 |
| 5.06 | 2-chlorophenyl | hydrogen | 4-methylphenyl | oil, NMR: 6.18 (s, 1H), 5.85 (d, 1H), 5.7 (d, 1H) |
| 5.07 | 2-chlorophenyl | hydrogen | 4-fluorophenyl | oil, NMR: 6.2 (s, 1H), 5.87 (d, 1H), 5.75 (d, 1H) |
| 5.08 | 2,4-dichlorophenyl | hydrogen | t-butyl | oil, NMR: 5.6 (d, 1H), 5.4 (d, 1H), 4.8 (s, 1H) 1.2 (s. 9H) |
| 5.09 | 2,4-dichlorophenyl | hydrogen | 4-fluorobenzyl | oil, NMR: 5.6 (d, 1H), 5.45 (d, 1H), 5.4 (t, 1H) 3.3 (d, 1H) |
| 5.10 | 2-methoxyphenyl | hydrogen | phenyl | 110–114 |
| 5.11 | 2-fluorophenyl | hydrogen | phenyl | 72–75 |
| 5.12 | 2-methylphenyl | hydrogen | phenyl | 72–75 |
| 5.13 | 2-bromophenyl | hydrogen | 4-fluorophenyl | 90–93 |
| 5.14 | 2-bromophenyl | hydrogen | 4-methylphenyl | oil, NMR: 6.18 (s, 1H), 5.72 (d, 1H), 5.85 (d, 1H) |
| 5.15 | 2-chlorophenyl | hydrogen | 4-t-butylphenyl | 125–130 |
| 5.16 | 2-bromophenyl | hydrogen | 4-t-butylphenyl | 145–150 |
| 5.17 | 2-chlorophenyl | hydrogen | t-butyl | oil, IR: 1482, 1435, 1100, 1054, 1040, 990, 771, 760, 717 |
| 5.18 | 2,4-dichlorophenyl | phenyl | phenyl | 160 |
| 5.19 | 2,4-dichlorophenyl | 4-fluorophenyl | phenyl | 180–183 |
| 5.20 | 2-bromophenyl | benzyl | phenyl | 132–135 |
| 5.21 | 2-bromophenyl | 2-chlorophenyl | phenyl | 127–130 |

TABLE 5-continued

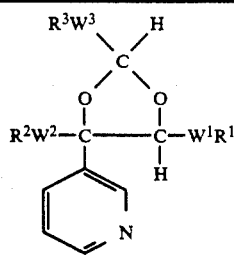

I (X + Y = —O—C(W³R³)—O—)
          |
          H

| No. | W¹R¹ | W²R² | W³R³ | Phys. data (mp. [°C.]; IR [cm⁻¹]; ¹H-NMR*) [ppm]) |
|---|---|---|---|---|
| 5.22 | 2-bromophenyl | 4-chlorophenyl | phenyl | oil, IR: 1490, 1417, 1090, 1062, 1026, 1017, 747, 737, 697 |
| 5.23 | 2,4-dichlorophenyl | 4-fluorobenzyl | phenyl | 155–157 |
| 5.24 | 2,4-dichlorophenyl | 2,4-dichlorobenzyl | phenyl | oil, IR: 1474, 1103, 1091, 1042, 1028, 991, 757, 712 |
| 5.25 | 2,4-dichlorophenyl | ethenyl | phenyl | oil, IR: 1474, 1091, 1069, 1053, 1027, 755, 711, 698 |
| 5.26 | 2-bromophenyl | ethenyl | phenyl | oil, NMR: 5.9 (s, 1H), 6.25 (s, 1H) |
| 5.27 | 2,4-dichlorophenyl | propen-3-yl | phenyl | oil, IR: 1477, 1418, 1091, 1069, 1039, 1028, 987, 761, 714 |
| 5.28 | 2,4-dichlorophenyl | isopropyl | phenyl | |
| 5.29 | 2,4-dichlorophenyl | cyclopropyl | phenyl | |
| 5.30 | 2-bromophenyl | cyclohexyl | phenyl | |
| 5.31 | 2-bromophenyl | 3-pyridyl | phenyl | |
| 5.32 | 2-cyclophenyl | 3-pyridyl | phenyl | |
| 5.33 | 2-chlorophenyl | isopropyl | phenyl | |
| 5.34 | 2-chlorothienyl | hydrogen | phenyl | |
| 5.35 | 3-bromothien-2-yl | hydrogen | phenyl | |
| 5.36 | 3-isopropyl-oxazol-5-yl | hydrogen | phenyl | |
| 5.37 | 3-phenylisoxazol-5-yl | hydrogen | phenyl | |
| 5.38 | 2-bromo-4-fluoro-phenyl | hydrogen | phenyl | |
| 5.39 | 2-chloro-4-fluoro-phenyl | hydrogen | phenyl | |
| 5.40 | hydrogen | isopropyl | phenyl | |
| 5.41 | hydrogen | isopropyl | 4-fluorophenyl | |
| 5.42 | hydrogen | isopropyl | 4-methylphenyl | |
| 5.43 | hydrogen | isopropyl | 4-chlorophenyl | |
| 5.44 | hydrogen | isopropyl | 4-methoxyphenyl | |
| 5.45 | 4-cyanophenyl | hydrogen | phenyl | |
| 5.46 | 4-methoximino | hydrogen | phenyl | |
| 5.47 | 2-bromophenyl | hydrogen | methyl | |
| 5.48 | 2-bromophenyl | hydrogen | chloromethyl | |
| 5.49 | 2-bromophenyl | hydrogen | methylthiomethyl | |
| 5.50 | 2-bromophenyl | hydrogen | methoxymethyl | |
| 5.51 | 2-bromophenyl | hydrogen | trichloromethyl | |
| 5.52 | isopropyl | hydrogen | phenyl | |
| 5.53 | methyl | hydrogen | phenyl | |
| 5.54 | cyclohexyl | hydrogen | phenyl | |
| 5.55 | pentyl | 4-fluorobenzyl | phenyl | |
| 5.56 | isopropyl | 4-fluorobenzyl | phenyl | |
| 5.57 | isopropyl | 4-fluorobenzyl | phenyl | |
| 5.58 | isopropyl | hydrogen | 4-fluorophenyl | |
| 5.59 | t-butyl | hydrogen | phenyl | |
| 5.60 | t-butyl | hydrogen | 4-methoximinophenyl | |
| 5.61 | 2-chlorophenyl | propynyl | phenyl | |
| 5.62 | 2-chlorophenyl | 2-pyridyl | phenyl | |
| 5.63 | 2-chlorophenyl | hydrogen | 4-methylcyclohexyl | |
| 5.64 | 2-trifluoromethyl | hydrogen | phenyl | |
| 5.65 | 2-bromophenyl | hydrogen | 1-naphthyl | |
| 5.66 | 2-chlorophenyl | 2-(4-chlorophenyl)eth-1-yl | phenyl | |
| 5.67 | 2-chlorophenyl | 1-(4-fluorophenyl)eth-1-yl | phenyl | |
| 5.68 | 2-bromophenyl | hydrogen | 2-nitrophenyl | |
| 5.69 | 2-bromophenyl | hydrogen | phenyl | NMR: 5.75 (d, 1H), 5.9 (d, 1H), 6.2 (s, 1H), 6.9–8.45 (m, 1H) |
| 5.70 | 2-bromophenyl | hydrogen | t-butyl | 100–103 |
| 5.71 | 2-chlorophenyl | ethenyl | phenyl | NMR: 5.55 (d, 1H), 5.75 (d, 1H), 5.9 (s, 1H), 6.2 (s, 1H), 6.65 (dd, 1H), 6.9–8.5 (m, 13H) |

*)in CDCl₃, TMS as internal standard

The N-oxides of the 3-substituted pyridines I may for instance be prepared by treating the compounds I with a peracid such as meta-chloroperbenzoic acid or peracetic acid, and then separating with aqueous NaHCO₃ solution the carboxylic acid which has formed.

Example 11

2-Phenyl-4-(3-pyridyl-N-oxide)-5-(2-methoxyphenyl)-1,3-dioxolane (compound no. 5.72)

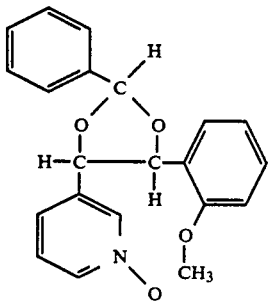

4.7 g (0.022 mol) of 80% strength meta-chloroperbenzoic acid is added to 150 ml of CH₂CL₂. A solution of 6.7 g (0.019 mol) of 2-phenyl-4-(3-pyridyl)-5-(2-methoxyphenyl)-1,3-dioxolane in 50 ml of CH₂Cl₂, and the whole is stirred for about 8 hours at room temperature. The precipitated metachlorobenzoic acid is filtered off, and the organic phase is washed twice with NaHCO₃ solution and twice with NaHSO₃ solution, and then dried over Na₂SO₄. A brown oil remains after evaporation of the solvent.

¹H-NMR (CDCl₃/TMS$_{int}$): δ/ppm=3.8 (s, 3H), 5.5 (d, 1H), 5.75 (d, 1H), 6.15 (s, 1H), 6.6–8.1 (m, 13H).

Use Examples

The comparative compounds employed were

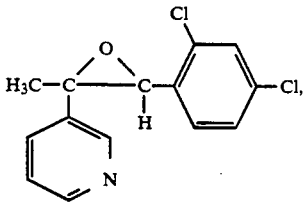  A disclosed in EP-A 074 018 (Example 9) and

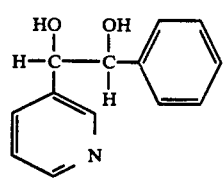  B

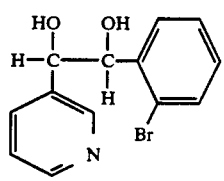  C

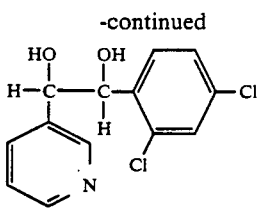  D

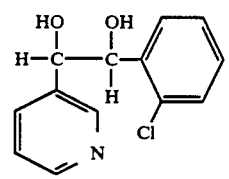  E

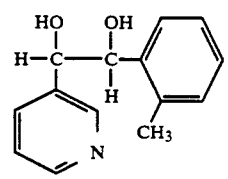  F disclosed in Tetrahedron 24, 1959 (1968).

Example 12

Action on Botrytis Cinerea in Pimientoes

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were inoculated with a spore suspension of Botrytis cinerea and kept at 22° to 24° C. in a chamber of 90 to 95% relative humidity. After 5 days the disease had spread to such an extent on the untreated control plants that the leaf necroses covered the major portion of the leaves.

The results from two independent experiments show that active ingredients 1.01, 2.03, 2.04, 3.06, 4.01 and 4.11, and 5.6, 5.7, 5.14 and 5.69, applied as 0.05 wt % spray liquors, have a good fungicidal action (83% and 80%) on Botrytis cinerea, whereas prior art comparative agents A, C and E do not exhibit any fungicidal action (0%).

Example 13

Action On Brown Rust Of Wheat

Leaves of pot-grown wheat seedlings of the "Kanzler" variety were dusted with spors of brown rust (puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with 0.025% aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients 1.01, 4.01, 4.02, 4.03, 4.04, 4.07, 4.08, 4.11, 4.20, 4.22, 4.25, 4.26 and 4.27, applied as 0.025 wt % spray liquors, have a very good action (98%) on brown rust, whereas comparative compound A has no fungicidal action.

Example 14

Action On Cucumber Mildew

Leaves of pot-grown cucumber seedlings of the "Chinesische Schlange" variety were sprayed at the two-leaf stage with a spore suspension of cucumber mildew (Erysiphe cichoracearum and Sphaerotheca fuliginea). After about 20 hours the plants were then sprayed to runoff with aqueous spray liquors containing (dry basis) 80% of active ingredient and 20% of emulsifier. After the sprayed-on layer had dried, the plants were set up in the greenhouse at from 20° to 22° C. and a relative humidity of 70 to 80%. To judge the action of the novel compounds, the extent of fungus spread was assessed after 21 days.

The results from two independent experiments show that active ingredients 1.01, 1.03, 2.03, 3.13, 3.18, 4.01, 4.02, 4.03, 4.04, 4.07, 4.08, 4.11, 4.18, 4.25, 4.27 and 4.30, and 5.6, 5.7, 5.9, 5.13, 5.14, 5.69 and 5.70, applied as 0.025 wt % spray liquors, have a better fungicidal action (97% and 90%) than prior art comparative compounds A (50%) and C, D and E (10%).

Example 15

Action On Pyrenophora Teres

Barley seedlings of the "Igri" variety were sprayed to runoff at the two-leaf stage with aqueous suspensions containing (dry basis) 80% of active ingredient and 20% of emulsifier. After 24 hours, the plants were inoculated with a spore suspension of the fungus Pyrenophora teres and placed for 48 hours in a high-humidity climatic cabinet at 18° C. The plants were then cultivated for a further 5 days in the greenhouse at 20° to 22° C. and a relative humidity of 70%. The extent of fungus spread was then determined.

The results show that active ingredients 5.2, 5.3, 5.6, 5.7, 5.12, 5.13, 5.14 and 5.69, applied as 0.05% spray liquors, have a better fungicidal action (90%) than prior art comparative agents C, D, E and F (10%).

Use Examples (herbicidal action)

The herbicidal action of the 3-substituted pyridines of the formula I is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed o the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

We claim:

1. Substituted pyridine of the formula I

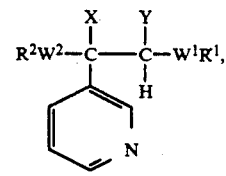

where the variables have the following meanings:
X and Y together are group

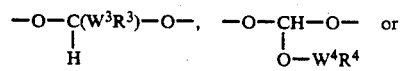

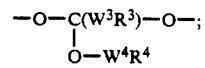

$W^1$-$W^4$ are each a direct bond or a group —CH$_2$—, —CH$_2$—CH$_2$—, —CH(CH$_3$)—, —CH$_2$O— or —CH$_2$S—, where the bond between the last two groups and the radicals $R^1$ to $R^4$ is via the oxygen or sulfur atom;

$R^1$-$R^4$ are each C$_1$-C$_6$-alkyl which may carry a C$_3$-C$_8$-cycloalkyl radical, or are each partially or completely halogenated C$_1$-C$_6$-alkyl, or are each C$_3$-C$_8$-cycloalkyl which may furthermore carry up to 3 C$_1$-C$_6$-alkyl groups, or are each C$_1$-C$_4$-alkoxy-C$_1$-C$_4$-alkyl, C$_1$-C$_4$-alkylthio-C$_1$-C$_4$-alkyl, C$_2$-C$_6$-alkenyl, C$_2$-C$_6$-alkynyl, phenyl or naphthyl, both of which may furthermore carry 1 or 2 of the following radicals: nitro, cyano, halogen, C$_1$-C$_4$-alkyl, partially or completely halogenated C$_1$-C$_4$-alkyl, C$_1$-C$_4$-alkoxy, C$_1$-C$_4$-alkoxyimino, phenyl or phenoxy each of which may, if desired, have from 1 to 5 halogen atoms on the aromatic moiety and the phenyl or naphthyl group may carry a number of halogen atoms, C$_1$-C$_4$-alkyl radicals, partially or completely halogenated C$_1$-C$_4$-alkyl radicals and/or C$_1$-C$_4$-alkoxy radicals such that the total number of radicals is 5;

the N-oxide and the plant-tolerated mineral acid salt and metal complex of I.

2. 3-substituted pyridines of the formula I as set forth in claim 1, where the variables have the following meanings:
X and Y together are group

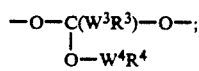

$W^1$-$W^4$ being a direct bond;
is 2,4-dichlorophenyl;
is C$_1$-C$_4$-alkyl, vinyl or halogenated phenyl;
$R^3$, $R^4$ are each methyl.

3. 3-substituted pyridines of the formula I as set forth in claim 1, where the variables have the following meanings:

X and Y together denote the group

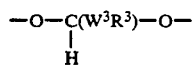

$W^1$–$W^3$ being a direct bond;
$R^1$ is 2-bromophenyl, 2-chlorophenyl or 2,4-dichlorophenyl;
$R^2$ is hydrogen and
$R^3$ is phenyl or 4-methylphenyl.

4. A fungicidal composition containing a solid or liquid carrier and a fungicidally affective amount of a 3-substituted pyridine of the formula I, an N-oxide thereof and/or a plant-tolerated salt or metal complex thereof as set forth in claim 1.

5. A method combating fungi, wherein a fungicidally effective amount of a 3-substituted pyridine of the formula I, or of an N-oxide or a plant-tolerated salt or metal complex thereof, is allowed to act on fungi, plants threatened by fungus attack, the habitat of such plants or on the seed of threatened plants.

* * * * *